United States Patent [19]

Jonas

[11] Patent Number: 4,674,337

[45] Date of Patent: Jun. 23, 1987

[54] PARTICLE DETECTOR

[76] Inventor: Otakar Jonas, 1113 Faun Rd., Wilmington, Del. 19803

[21] Appl. No.: 882,399

[22] Filed: Jul. 7, 1986

[51] Int. Cl.$^4$ .................. G01N 15/02; G01N 15/07; G01F 1/28
[52] U.S. Cl. .................. 73/861.73; 73/61 R; 73/861.21
[58] Field of Search .............. 73/587, 32 A, 61 R, 73/861.21, 861.73

[56] References Cited

U.S. PATENT DOCUMENTS

| | | | |
|---|---|---|---|
| 3,841,144 | 10/1974 | Baldwin | 73/61 R |
| 3,906,780 | 9/1975 | Baldwin | 73/61 R |
| 4,135,395 | 1/1979 | Sullivan et al. | 73/861.21 |
| 4,149,415 | 4/1979 | Harbour | 73/432 |

FOREIGN PATENT DOCUMENTS 1435972  5/1976  United Kingdom .

Primary Examiner—Howard A. Birmiel
Attorney, Agent, or Firm—Dean R. Rexford

[57] ABSTRACT

A device for estimating the number and the mass of particles borne in a fluid stream comprises a novel target on which the particles impact at a constant angle thereby generating acoustic signals proportional to the kinetic energy of the particles. The acoustic signals are converted by means of a transducer to corresponding electric signals which are processed by art computer means. Compensating probes are disclosed for subtracting extraneous noise.

4 Claims, 2 Drawing Figures

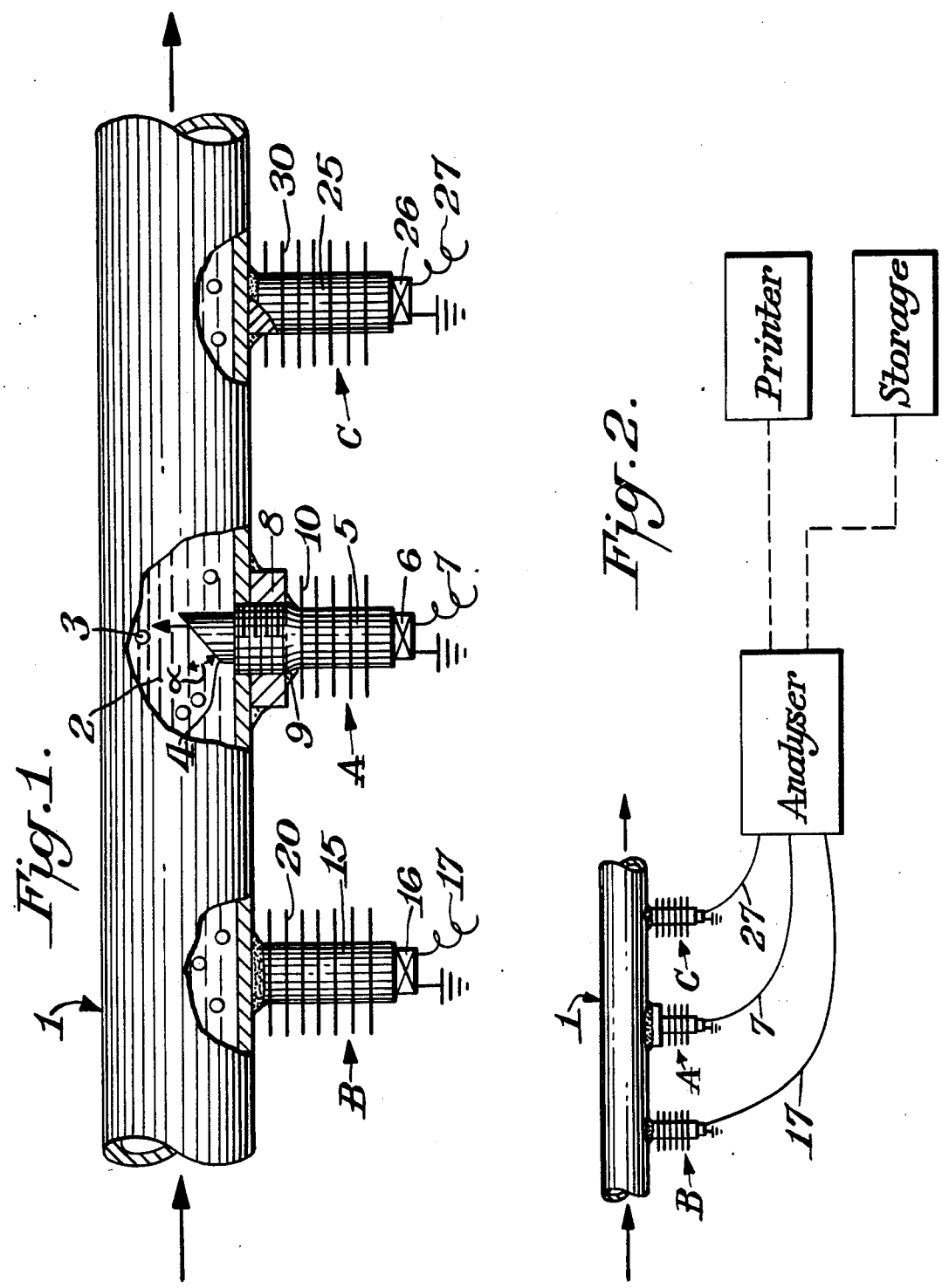

PARTICLE DETECTOR

BACKGROUND OF THE INVENTION

1. Field of the Invention

This invention relates to, and has as its principal object, the provision of a novel device for measuring by acoustic means, the number and mass of individual particles borne in a fluid stream. Particular application of the invention is seen in the detection and characterization of particles in steam, especially superheated steam, water droplets in steam, dirt in an air stream, and particles in flue gases.

2. Prior Art

British Patent specification No. 1,435,972 teaches a device for detecting the presence of particulate material in a fluid stream flowing in a conduit. The device, which is directed to the detection of sand in crude oil and natural gas streams, comprises an acoustical detector disposed in the conduit. The detector, having a resonant frequency in excess of 100 kHz, produces an output signal corresponding to the vibratory energy produced by particle impact on the detector. The detector comprises a piezoelectric transducer confined in a cylindrical probe filled with oil. The probe is placed at right angles to the stream.

U.S. Pat. No. 4,149,415 teaches a device for distinguishing wheat grains from a mixture of straw and chaff. The device comprises a flat plate target disposed at right angles to the stream of particles in air. Attached to the downstream side of the plate are transducers inter alia which generate electrical signals corresponding to particle impacts on the plate. Resultant signals are electronically processed whereby to distinguish grain from straw and chaff. Spurious signals are suppressed electrically and transducers are mounted with opposite polarities whereby fundamental and odd harmonic modes cancel out.

The patent teaches against the use of a prior art cylindrical probe because the sensitivity varies across the width of the cylinder due to variation in the impact angle.

SUMMARY OF THE INVENTION

A device for monitoring the number and mass of individual particles borne in a flowing fluid stream of predetermined flow rate comprising:

(a) a target in said stream whereon an essentially constant predetermined fraction of said particles impact, said target being flat and so oriented as to cause said particles to impact on said target at essentially the same angle whereby to produce acoustic signals proportional to the kinetic energy of the particles, and discourage accumulation of particles on said target;

(b) means for transmitting said acoustic signals out of said stream;

(c) means outside said stream for converting said acoustic signals to corresponding electric signals; and (d) electronic means responsive to said electric signals for processing said signals whereby to provide an estimate of the total number and the mass of individual particles.

BRIEF DESCRIPTION OF THE DRAWINGS

FIG. 1 shows a conduit confining a fluid stream containing particles and, in assembly A, passing through the wall of said conduit, an impact detecting probe of the invention comprising a target. Optional assemblies B and C are compensating probes which do not pass through the conduit wall.

FIG. 2 is a diagram showing schematically the cooperation of the probes of FIG. 1 with electronic means for processing the signals generated by piezo-electric transducers at the probes.

DESCRIPTION OF THE PREFERRED EMBODIMENTS

Turning now to FIG. 1, one sees a pipe conduit 1 carrying a fluid stream 2 such as steam, water, or air, said stream moving, as indicated in the drawing, from left to right. The stream contains particles 3 such as spalled metal oxide products or say water droplets in a stream of steam, or dirt in a stream of air. in connection with assembly A, it is seen that some of the particles 3 strike target 4, an eliptical surface, thus elastically deforming it and generating acoustic signals in the 100 to 900 kHz range. The impact angle, $\alpha$, is essentially constant. Said signals are transferred via cylindrical detecting probe 5 to piezo-electric transducer 6 which converts the acoustic signals to electrical signals. The signals are brought to the electronic analyzer of FIG. 2 via ground and lead 7.

Cylindrical probe 5 in this embodiment is secured by threads in boss 8 which is welded to conduit 1. A tight fit is providd by seal weld 9. Other means, as will occur to the artisan, are operable.

Fins 10 are optional and are not needed in moderate temperature applications. However, in high temperature service, for example when the conduit carries superheated steam at 540° C., the fins are useful for dissipating heat so as not to overheat transducer 6.

Assemblies B and C are optional compensating probes. They do not pass through the wall of conduit 1 but are instead, in this embodiment, welded thereto. The components of assembly B are assigned numbers corresponding to those of assembly A to which 10 is added; in assembly C, 20 is added.

The materials employed in the probe assemblies are selected to possess mechanical and chemical stability appropriate to the circumstances of their use. Common metals and alloys are operable. Preferred for many uses are brass, bronze, titanium, and alloy steel. Most preferred are stainless steels. The metals and alloys should preferably not undergo plastic deformation and should not excessively damp the acoutic signals generated by impact of the monitored particles.

The target (component 4) of the detecting probe is a surface so arranged as to intercept particles at a constant angle thus generating acoustic signals which are proportional to the kinetic energy of the particles, without accumulating particles thereon. In this invention this result is accomplished by presenting a target surface to the flowing fluid stream which at all points makes a fixed angle $\alpha$ with the axis of the stream. The preferred angles are from about 20° to about 60°, about 40° being most preferred. It is convenient to provide a flat eliptical surface as shown in FIG. 1 by machining a flat surface on a piece of cylindrical stock at the selected angle. Other methods will occur to the machinist. Small angles are selected if particles tend to collect on the surface; larger angles if greater sensitivity is needed. Further, depending on the nature of the particles, it may be desirable to polish the surface and/or to deposit on the target a hard material such as a stellite alloy.

The target can also comprise more than one surface, so long as all particles strike it at essentially the same angle; for example, the target may have the form of a wedge.

Transducers 6, 16, and 26 are commercially available acoustic emission piezo-electric transducers normally in a housing comprising a wear plate. They may have a resonant frequency in the range of 100 to 900 kHz. The resonant frequency is normally selected to be generally outside the noise frequencies of the monitored system. Such transducers are sold by Physical Acoustics Corporation, Princeton, N.J., among others. The wear plate of the transducers is elastically coupled, e.g. by means of adhesive or heavy grease, to the end of the cylinder cylindrical probe.

Turning now to FIG. 2 one sees schematically the cooperation of invention assembly A with assemblies B and C, an art analyser and associated printing and storage devices.

The Physical Acoustics Corporation offers sophisticated analysers called the Series 3000 Acoustic Emission Analysers. Such analysers are capable inter alia of substracting extraneous noise signals detected by the compensating probes from the signal generated by a detecting probe of the invention. Such systems are especially useful in monitoring steam lines, for example.

The Physical Acoustic Emission Corporation also offers a less sophisticated one-probe analyser called the Count Rate Analyser Model 4300. This device has a built-in band of eight electronic filters, total amplification of 100 dB and three signal processors which produce DC voltage signals proportional to the energy, and the number of impacts. The analyser also comprises a clock allowing monitoring as a function of time, and a variable threshold for each parameter.

In as much as the target occupies a fixed and measurable fraction of the cross sectional area of the conduit, it follows semiquantitatively that the number of impacts on the target over time will be a constant calculable fraction of the total number of particles passing through the conduit. Most monitored particles, being substantially more dense than the fluid, are not deflected around the target by the fluid flow around the target.

The combination, of which the invention detecting probe is a part, is capable not only of counting the total number of particles striking the target as set out above but can also, following calibration, estimate the mass of the individual particles by means of the amplitude of the impact signals. Calibration can be carried out in a number of ways. For example, a simple pendulum, say a steel shot of known mass attached to a string of negligable mass is allowed to fall through a known arc and strike the probe of an isolated detecting probe at the angle employed in service. From classic physics the kinetic energy, $\frac{1}{2} mv^2$, is calculated knowing the potential energy, mhg, where m = the mass of the shot; h = the height of the shot above the target; g = the gravitational constant; and v is the calculated impact velocity. Knowing the velocity of the stream, which includes the particles, by art measurement means outside the invention, the mass of the particles can be computed. Other calibrating means such as allowing a ball of known mass to strike the target after rolling down a tube from a known height will occur to the engineer.

Although compensating probes are not absolutely necessary to operability, it is preferred to employ at least one, preferably situated upstream from the detecting probe. It is, however, most preferred to employ two compensating probes, one upstream and one downstream from the detecting probe, as shown in FIG. 2.

The distance apart may vary with the application. In superheated steam service employing a cylindrical conduit a uniform distance between probes of about four diameters or at least about 12 inches (30.5 cm) to give adequate time between signals is preferred.

That which is claimed is:

1. A device for monitoring the number and mass of individual particles borne in a flowing fluid stream or predetermined velocity comprising:
    (a) a target in said steam whereon an essentially constant predetermined fraction of said particle impacts, said target being flat and so oriented as to cause said particles to impact on said target at essentially the same angle in the range of 20° to 60° whereby to produce acoustic signals proportional to the kinetic energy of the particles, and discourage accumulation of particles on said target;
    (b) means comprising a cylindrical probe for transmitting said acoustic signals out of said stream;
    (c) means outside said stream for converting said acoustic signals to corresponding electric signals;
    (d) electronic means responsive to said electric signals for processing said signals whereby to provide an estimate of the total number and the mass of the individual particales.

2. The device of claim 1 wherein the cylindrical probe and target are fabricated from a metal selected from the group consisting of brass, bronze, titanium and alloy and stainless steel.

3. A device for monitoring the number and mass of individual particles borne in a flowing stream of predetermined velocity comprising:
    (a) a target in said stream whereon an essentially constant predetermined fraction of said particles impacts, said target being flat and so oriented as to cause said particles to impact on said target at essentially the same angle in the range of 20° to 60° whereby to produce acoustic signals proportional to the kinetic energy of the particles, and discourage accumulation of particles on said target;
    (b) means comprising a cylindrical probe for transmitting said acoustic signals out of said stream;
    (c) means outside said stream for converting said acoustic signals to corresponding electric signals;
    (d) electronic means responsive to said electric signals for processing said signals whereby to produce as estimate of the total number and the mass of the individual particles; and
    (e) one to two compensating probes cooperating with the electronic means of (d) to subtract out extraneous noise signals.

4. The device of claim 3 wherein the cylindrical probe and target are fabricated from a metal selected from the group consisting of brass, bronze, titanium and alloy, and stainless steel.

* * * * *